United States Patent [19]

Schobel et al.

[11] Patent Number: 4,719,181

[45] Date of Patent: Jan. 12, 1988

[54] FREE FLOWING GRANULAR INDICATOR MATERIAL FOR PEROXIDASE-LIKE ACTIVITY

[75] Inventors: Alexander M. Schobel, North Plainfield; Raymond L. Mohrle, Denville, both of N.J.

[73] Assignee: Warner-Lambert Company, Morris Plains, N.J.

[21] Appl. No.: 811,579

[22] Filed: Dec. 20, 1985

[51] Int. Cl.$^4$ ...................... G01N 33/52; G01N 33/72
[52] U.S. Cl. .................... 436/66; 252/174.13; 252/363.5; 422/57; 422/61; 427/3; 427/212; 428/403; 436/166; 436/904
[58] Field of Search ................ 436/66, 166, 904; 422/57, 61; 435/28; 252/174.13, 381, 384, 363.5; 427/3, 212, 215, 220; 428/403

[56] References Cited

U.S. PATENT DOCUMENTS

| | | | |
|---|---|---|---|
| 3,282,728 | 11/1966 | Lacroux et al. | 427/220 |
| 3,356,526 | 12/1967 | Waldman et al. | 427/212 X |
| 3,402,137 | 9/1968 | Fischer et al. | 252/363.5 X |
| 3,455,714 | 7/1969 | Bishop et al. | 252/363.5 X |
| 3,769,222 | 10/1973 | Yurko et al. | 252/174.13 |
| 3,997,470 | 12/1976 | Monte et al. | 436/66 |
| 4,177,254 | 12/1979 | Khan et al. | 427/3 X |
| 4,417,999 | 11/1983 | Duffy | 252/384 X |

FOREIGN PATENT DOCUMENTS

| | | | |
|---|---|---|---|
| 0085261 | 8/1983 | European Pat. Off. | 422/58 |
| 0121317 | 10/1984 | European Pat. Off. | 435/28 |
| 2706690 | 8/1978 | Fed. Rep. of Germany | 436/166 |
| 0163324 | 9/1984 | Japan | 427/212 |

Primary Examiner—Barry S. Richman
Assistant Examiner—Robert J. Hill, Jr.
Attorney, Agent, or Firm—Howard Olevsky; Gary M. Nath

[57] ABSTRACT

A test reagent system and method for detecting the presence of peroxidase-like activity is provided by the present invention. The reagent system comprises a free-flowing granular indicator material comprising a granular substrate such as sorbitol or mannitol having coated thereon gum guaiac and an aqueous organic reagent solution containing water, an organic solvent, an oxidizing agent being capable of oxidizing the indicator material in the presence of peroxidase-like activity, and a buffer.

16 Claims, No Drawings

FREE FLOWING GRANULAR INDICATOR MATERIAL FOR PEROXIDASE-LIKE ACTIVITY

BACKGROUND OF THE INVENTION

This invention relates to a composition useful for the detection of peroxidase-like activity and in particular to the identification of peroxidase-like activity in various specimens. More particularly the invention relates to the preparation of a granular indicator material which when admixed with a separate reagent solution, is useful for the detection of peroxidase-like activity present in stool or biological fluids.

The detection of perioxidase-like activity has become an invaluable aid to the medical practitioner for the diagnosis of a number of disorders. One of the most widely used indicator reagents for diagnosing occult blood is derived from an extract from the wood of certain species of trees of the Guaiacum genus native to the American tropics. The extract, termed guaiac, turns from essentially colorless to blue in the presence of hemoglobin and an oxidizing agent such as hydrogen peroxide. More specifically, the guaiac reagent is sensitive to what is termed "peroxidase-like activity" which results from the combination of an oxidizing agent with hemoglobin or certain chemically similar compounds.

Over 100,000 persons in the United States are affected by cancer of the colon and rectum per year, occurring equally in both the male and female population. When the number of colorectal cancers occurring each year is combined with the number of cancers occurring in other digestive organs, including the esophagus and stomach, such cancers of the digestive system account for more occurrences of cancer than any other single form of the disease. Contrary to many other forms of cancer, early diagnosis and treatment of digestive tract cancer does result in a cure rate of 80% to 90% of those persons affected by the disease. If, however, the disease is not detected until the later stages, the cure rate can drop drastically to 25% or less. Thus, early detection of the disease is critical to successful treatment of digestive tract cancer.

Most, but not all, cancers of the digestive tract bleed to a certain extent. Some blood found in the gastric contents and in vomitus is indicative of conditions associated with disorders of the mucous membrane, such as ulcers, diverticulitis, colitis, and carcinoma. In contrast, some blood is deposited on and in fecal matter excreted from the digestive system. The presence of blood in fecal matter is not normally detected, however, until gross bleeding occurs, resulting in blood visible to the naked eye. Gross bleeding, however, does not normally occur until the digestive tract cancers are in advanced stages.

It is known that digestive tract cancers in the early stages also tend to bleed, giving rise to occult (hidden) blood in fecal matter. Test equipment and test procedures have been developed for use by physicians in testing for the presence of occult blood in fecal matter. One of the most successful tests is manufactured and sold by SmithKline Diagnostics of Sunnyvale, Calif., under the trademark "Hemoccult". The package for the "Hemoccult" test is disclosed in U.S. Pat. No. 3,996,006 issued to J. F. Pagano. Briefly, the Pagano test employs an absorbent white paper impregnated with a guaiac reagent encased in a special test slide having openable flaps on both sides of the test slide. To use the Pagano test slide, one must obtain a sample of fecal matter, smear it onto the guaiac-impregnated paper by opening the panel on one side of the test slide, and thereafter close the panel. A panel on the opposite side of the test slide is then opened and a developing agent, which is a stabilized solution of hydrogen peroxide and denatured alcohol, is applied to the guaiac-impregnated paper. If occult blood is present in the fecal matter smeared on the opposite side of the paper, the product of the guaiac reaction will appear as a blue substance against the white paper background, providing a positive indication of the presence of blood in the fecal matter.

Although the Pagano test is excellent for use by physicians in their offices and by diagnostic laboratories, it is not the type of test that is readily adaptable for use by the ordinary person because of his adverse reaction to handling fecal matter and because of his lack of skill in interpreting the results. As stated above, the Pagano test requires that a specimen of fecal matter be obtained. Normally, a specimen is obtained by procuring a sample on the end of a spatula or a wooden tongue depressor, which is then used to smear the specimen on the paper in the Pagano test slide. Once the sample is obtained and the test procedure completed, both the test slide and the spatula or depressor must be disposed of. Disposal of the used materials can and does present a physical problem to, if not an adverse psychological reaction for, the ordinary person. Thus, the ordinary person is not likely to use the Pagano test because of its unclean nature and because of the disposal problems associated with the used test slide and spatula or depressor. Additionally, the ordinary person does not necessarily have the skill required to analyze, and thus form accurate conclusions from the test results.

As an alternative, the ordinary person can initiate the Pagano test in his home and then forward the test slide to his physician or a laboratory for addition of the developing agent and analysis of the test. This procedure, however, requires cold storage of the test slide and specimen if there is a significant time lapse before the test can be completed. Certainly, the ordinary person does not wish to store a fecal specimen in his household refrigerator, normally the only cold storage available to him, until he can present the specimen to his physician or an appropriate laboratory. Thus, the general public is not likely to follow or comply with this alternative.

Another test for occult blood is suggested by D. E. Fonner in U.S. Pat. No. 2,838,377. The Fonner test, as disclosed, can be effected in a toilet bowl containing fecal matter. The basic test reagents employed by Fonner are o-tolidine and benzidine. These reagents in the presence of blood and other reactants produce a dye visible to the naked eye. Although the Fonner test appears to be a solution to the problem of finding a viable home test for occult blood, it has not met with success for two reasons. First, the above-listed reagents are in themselves known to cause cancer and thus are not suitable for general public distribution. More importantly, the Fonner reagents have a relatively high rate of providing false indications of the presence of occult blood as a result of tap water impurities.

Nicholls and Fonner disclose in U.S. Pat. No. 2,799,660 an occult blood test using a tablet composition containing a blood indicator, oxidizing agent, acetate compound and water-soluble solid acid. The tablet may additionally contain an effervescent agent. This test is being marketed by Ames under the trademark "Hematest". In determining the presence of absence of occult blood in a sample of urine a drop of the urine specimen is placed on a piece of dry filter paper, and when the drop has soaked into the paper a tablet prepared as above described is placed in the center of the drop and then two drops of water added to the tablet. With a positive test a ring of color appears on the filter paper surrounding the tablet, the color ranging from a very faint to a very deep blue, depending upon the concentration of blood in the sample.

To date, the use of the Pagano test, the Fonner test, and other similar tests has been limited primarily to physicians and diagnostic laboratories. Although this limitation might not at first glance present a significant problem, it does limit the early detection of digestive tract cancers, primarily because patients will not see a physician until other symptoms of digestive tract cancers, such as gross bleeding, manifest themselves. Thus, early detection of cancer of the digestive tract still does not occur with the great majority of patients who contract the disease.

While the prior art has recongnized the need for a simple and reliable test for detection of peroxidase activity, such test has not been available for routine home usage in an acceptable format.

SUMMARY OF THE INVENTION

The present invention provides a reagent system which is useful for the in-home detection of peroxidase-like activity. The reagent system comprises free-flowing granular indicator material which when admixed with an aqueous-organic reagent solution results in the formation of a stable, visible indicator for the presence of peroxidase-like activity, such as the presence of hemoglobin in a particular specimen or sample. The composition in the presence of peroxidase acivity, such as blood, develops a visible color change. The reagent system, that is the granular indicator and reagent solution used to prepare it are stable at room temperature and are easily used in an acceptable manner rendering it effective for home usage. The reagent system of the invention comprises two main components: (a) a free-flowing granular indicator material; and (b) an aqueous-organic reagent solution containing an organic solvent for solubilizing the indicator, an oxidizing agent capable of oxidizing the indicator material in the presence of peroxidase-like activity, a buffer, and water.

The invention also contemplates a method for the detection of peroxidase-like activity and kit for use thereof which include (1) collecting a specimen to be analyzed for the presence of peroxidase-like activity; (2) contacting the specimen, with a composition prepared by admixing (a) a free-flowing granular material containing about 1% to about 30% indicator and (b) an aqueous-organic reagent solution containing an organic solvent, an oxidizing agent being capable of oxidizing said indicator material in the presence of peroxidase-like activity, a buffer and water; and (3) detecting the presence or absence of peroxidase-like activity.

DETAILED DESCRIPTION OF THE INVENTION

The instant inventive concept, like those of the prior art, are based on the detection of peroxidase-like activity present in stool and biological fluids. This peroxidase-like activity, also preferred to as catalytically active substances, in the case of blood, has been associated with the presence of hemoglobin. These substances belong to the general class of hemoproteins and conjugate proteins all of which have the same prosthetic group, iron protoporphyrin or heme. This prosthetic group has the ability to catalyze the transfer of oxygen from an oxygen source to an acceptor which in turn becomes oxidized. The acceptor is a colorless precursor until it becomes oxidized wherein the oxidized form indicates the presence of the peroxidase-like activity by color formation.

The reagent system of this invention has enabled the preparation of an in-home diagnostic test for peroxidase-like activity, such as occult blood in stool using a free-flowing granular indicator material containing gum guaiac, which is stable for long periods of time in the dry form and which, in combination with an aqueous-organic reagent solution, is likewise stable for long periods of time.

The instant invention represents a significant advance in the art by the preparation of a stable diagnostic reagent system which contains all of the essential materials necessary for the detection of peroxidase-like activity. This composition is used by merely contacting the specimen to be analyzed with the reagent system solution prepared by dissolving the granular indicator in the aqueous-organic reagent solution in one simple step and avoids the prior art manipulative handling of multiple reagents and specimens.

The granular indicator material is intended for use at the time a test is to be performed and results in the formation of a stable aqueous-organic reagent solution that is additionally stable for at least 9 months. The indicator material in addition to being stable, must be capable of rapid dissolution in the aqueous-organic reagent solution. Rapidity of dissolution is essential to prepare a detection solution which is used within fifteen minutes after being admixed in order to result in consistent and uniform detection of occult blood without the formation of false negative results. In this regard it has been found to be essential to prepare a granular composition which contains the indicator material.

The indicator of this invention is gum guaiac which is capable of accepting oxygen and being oxidized to a colored dye in the presence of the oxygen source. As used herein, the term gum guaiac includes resin guaiac; individual components of resin guaiac such as alpha-guaiaconic acid, beta-guaiaconic acid, guaiacic acid and related compounds, guaiaretic acid and guaiacin; and mixtures thereof. This material is preferred because of its recognition as an effective indicator, its non-carcinogenicity and commercial availability. In the presence of an oxygen source and peroxidase-like activity, guaiac changes from colorless to a blue color.

Gum guaiac normally exists as a powdered material which is not free-flowing. It is insoluble in water but soluble in the solvents used in the organic reagent solution. When gum guaiac powder per se is added to the aqueous organic reagent solution it tends to agglomerate and adhere to the walls of the container holding the reagent. These agglomerates first solubilize on the outside retaining a dry, solvent unimpregnated inner core. Thus there are formed soluted lumps which are only slowly penetrated by the reagent solution. As a result, gum guaiac powder solubilizes in the aqueous organic reagent solution in excess of two minutes.

It has been unexpectedly found that gum guaiac possesses film-forming properties and can be employed as a coating upon other materials. According to the invention gum guaiac can be made to solubilize in the organic reagent solution in thirty seconds or less by coating it on a compatible granular substrate material which is free-flowing, soluble in the organic reagent solution and non-interfering with the reactions occurring in the determination of peroxidase-like activity. The resulting coated granular material is a free-flowing granular indicator material.

The amount of gum guaiac employed in the granular material of the invention is dependent upon the sensitivity desired, that is the extent of color change evidenced from the oxidation reaction. Generally, the amount of gum guaiac in the total granular substrate material should constitute between 1.25% to 30% by weight and the coated material should constitute from 98.75% to 70% by weight. Preferred useful amounts will vary but should be consistent to yield from about 0.01% to about 3.0% and preferably about 0.25% to about 2.0% by weight of indicator, based upon the weight of the total reagent solution when dissolved. Amounts above about 3% are not desired since they may result in hypersensitivity showing false positive results. Amounts below about 0.01% are not recommended since they do not provide sufficient color development for accurate detection of peroxidase-like activity.

In order to assure rapid dissolution of the indicator in the organic reagent the size of the free-flowing granular indicator should be between about $-12$ and $+120$ mesh and preferably between $-20$ and $+60$ mesh (U.S. Standard Size). Granulation weights of about 0.1 grams to about 1.5 grams and preferably 0.3 grams to about 0.75 grams based upon 15.0 ml. of reagent solution have been found suitable for use in the invention.

Granular indicators of the invention when prepared with gum guaiac as the indicator material may contain additional additives to aid in their stability, dispersivity and rapidity of dissolution.

The granular substrate material coated by gum guaiac must itself be free-flowing, compatible with the gum guaiac in solution and soluble in the organic reagent solution. Its particle size as a coarse powder should be between 20 and 100 mesh and preferably between 20 and 60 mesh. Particularly preferred as the granular material is sorbitol and mannitol.

The free-flowing granular indicator is preferably prepared by coating the granular material with gum guaiac by spray coating in a fluidized bed apparatus. Pan coating may also be employed.

In the fluidized bed coating procedure the granular substrate material is employed as the solid feed and a solution in a solvent such as ethanol for example containing gum guaiac and other additives which will be discussed hereafter is employed as the spray solution. Spraying may be concurrent or counter-current. The inlet temperature of the fluidized bed coating may vary depending upon the spray solution atomization, air flow and solution flow rate. Generally the temperature may vary between 30° and 50° C. The solution temperature can vary between ambient temperature up to the flash point of the solvent. Outlet temperatures should vary from about 20° to 30° C. The spray solution should contain from about 60% to 95% solvent and from about 5% to 40% gum guaiac.

As an additional additive it is preferred to employ an antistatic agent in the coating which functions to provide a sink for static charges resulting from particle to particle interaction. The antistatic agent must also be soluble in the spray solution solvent. The amount of antistatic agent employed in the granular indicator should be sufficient to be effective but not so high as to cause agglomeration of the gum guaiac. Generally the antistatic agent should comprise from about 1% to 3% by weight of the solution in which case the gum guaiac should comprise from 2% to 39% by weight, the remainder being solvent. When incorporated into the granular indicator it should comprise from 0.25% to 2% by weight of the granular indicator.

The preferred antistatic agents are quaternary ammonium compounds that are soluble in water and alcohol. Exemplary compounds are stearyl dimethyl benzyl ammonium chloride, bis-(2-hydroxy-ethyl) octyl methyl ammonium para-toluene sulfonate, mink-amidopropyl dimethyl hydroxy-ethyl ammonium chloride, tetradecyl trimethyl ammonium bromide and PEG-15 tallow polyamine. (The latter being Polyquart H, a trademark product of Henkel Chemicals).

In order to improve the flow and stability of the granular indicator a glidant is added to the granular indicator after spray coating of the gum guaiac on the granular substrate. For this purpose, it is essential that the coated substrate be dried at an elevated temperature, e.g. 65° C. to render the gum guaiac tacky to ensure glidant adhesion.

The preferred glidant is submicron size talc which is a highly purified magnesium silicate. The minimum particle size should be about 200 mesh and preferably about 325 mesh. Other useful glidants include microcrystalline cellulose, powdered cellulose, calcium silicate, corn starch, sodium benzoate, and calcium carbonate of the same particle size. Materials such as coarse calcium carbonate, fumed silica, polytetrafluoroethylene and silica are not suitable glidants because they cause static charges to be produced or demix when blended with the guaiac coated particle and will not adhere to the granules. When employed the glidant should comprise from 0.5 to 10% by weight of the total granular indicator.

In pan coating, the granular substrate is placed in a rotating pan and a solution of the gum guaiac in a solvent with antistatic agent is added at elevated temperatures but below the flash point of the solvent until the substrate is coated. Thereafter the coated substrate is heated as above to render the gum guaiac coating tacky and the glidant subsequently mixed therewith. In still another alternative, a preblend of gum guaiac and granular substrate material is formed with or without antistatic agent to which a solvent such as ethanol is added. After mixing and drying the glidant is added as above.

The reagent solution of the invention contains several essential ingredients: an organic solvent capable of solubilizing the indicator material, an oxidizing agent capable of oxidizing the indicator material in the presence of peroxidase-like activity, a buffer to maintain the pH value of the solution, and water. This solution should be separately storage stable for up to at least 24 months prior to admixing with the granulated indicator material.

The organic solvent is present in the formulations of this invention to stabilize the oxidizing agent and to facilitate dissolution of the indicator material. A wide range of organic solvents may be used which are nonreactive with the formulation ingredients and which are preferably miscible in water.

Representative organic solvents include compounds selected from (1) alcohols, such as methanol, ethanol, propanol, isopropanol and isobutanol; (2) ketones, such as acetone, and mixtures thereof. Most preferred solvents are selected from the group consisting of methanol, ethanol, isopropanol and mixtures thereof.

The amount of solvent employed is that amount which is sufficient to keep the gum guaiac in solution. This amount may vary widely and preferable ranges in amounts up to 75% by weight preferably 40–70% by weight of the total formulation are useful. The exact amount of solvent for a particular formulation can be readily determined since it is that amount which is added to the remaining ingredients to yield a 100% solution.

The amount of water present in the solution will vary widely but must be sufficient to dissolve the oxidizing agent and buffer in order to maintain the pH value of the reagent solution. As such the aqueous-organic reagent solution may contain from about 5% to about 45% water and about 95% to about 55% organic solvent.

The oxidizing agent is selected from hydrogen peroxide or materials that will yield hydrogen peroxide in the presence of water and are stable in the presence of the solvent. Hydrogen peroxide is the oxidizing agent that promotes the reaction between the indicator and the peroxidase-like activator to produce the indicator's color change. The oxidizing agent must be capable of reacting with the indicator only in the presence of the peroxidase-like activity containing material and remain stable in the formulation during storage.

Representative oxidizing agents include both organic and inorganic peroxides. Illustrative compounds include hydrogen peroxide, urea peroxide, potassium persulfate and mixtures thereof.

The oxidizing agent is employed in amounts of about 0.15% to about 3.0% by weight, based on the weight of formulation, and preferably from about 1.0% to 2.0% by weight. Higher amounts are not preferred since they may result in premature oxidation of the indicator after the indicator is added and possible precipitation of ingredients during storage whereas lower amounts will not enable sufficient oxidation for visual detection, possible slow reactivity and loss of peroxidase-like activity.

A buffer is employed in the formulation to aid in stability and to provide the optimum pH value to enable catalytic activity to occur. It is essential that the buffer selected maintain the pH within a range in which the indicator material changes color upon oxidation. Normally this will be between a pH of about 2 and about 8 and preferably between about 3.5 and about 6.5. Higher pH values should be avoided to prevent autoxidation of the indicator resulting in false positive results. Lower pH values do not result in efficient oxidation.

Representative buffers include citrate, tartrate, phosphate, acetate and mixtures thereof with citrate being preferred.

The aqueous-organic reagent solution of the invention may be prepared by routine procedures. The exact manner of mixing the reagents is not critical.

As will be readily recognized by one of ordinary skill, the present invention represents a significant advance of the prior art diagnostic aids employing reagent impregnated papers. All that need be done with the reagent system defined herein, is to dissolve the free-flowing granular reagent containing the indicator materal in a bottle containing the aqueous-organic reagent solution. The granular reagent will dissolve in the reagent solution in thirty seconds or less. The resulting solution is then placed onto the contents to be tested for peroxidase-like activity and to observe the composition for the characteristic color change. The diagnostic aid and method for determining the presence of hemoglobin, such as in stool, through peroxidase-like activity in accordance with the present invention does not require the conventional handling of specimen, such as feces and can be simply performed in the home without need for professional interpretation of results.

In accordance with the present invention, a single container may be employed containing all of the test reagents, which when admixed with the indicator and placed in contact with the specimen result in a characteristic color change resulting from the indicator oxidation reaction. This container is thus useful in a diagnostic kit for the detection of peroxidase-like activity.

The reagents may be dispensed in any convenient manner. Conventional dispensing means can include dropper bottle, spray delivery systems and aerosol delivery systems. Alternatively, conventional thickening additives may be employed in sufficient quantities to enhance thixotropy of the solution. Such solution can then be dispensed by roller means, dropper means and/or conventional physical manipulation. Such thixotropic additives may include but are not limited to silica gels, polyethylene glycol, methylcellulose, polyvinyl alcohol, poly(ethylene oxide) and quaternary ammonium derivatives.

The specimen may be obtained by routine collection procedures. Without being limited thereto, such procedures include standard techniques for isolating fecal occult blood, hemoglobin, biological fluids and so forth. The term biological fluids as used herein includes salvia, urine, gastric fluids, vaginal secretions and cervical secretions. Such specimens may be obtained using standard adsorptive materials including paper strips and wood products. The actual method for collecting the specimen is considered to represent standard well-known technology readily available to those skilled in the art.

The following examples are given to illustrate the invention, but are not deemed to be limiting thereof. All percentages given throughout the specification are based upon weight unless otherwise indicated.

EXAMPLE I

This example demonstrates the preparation and use of a free-flowing granular indicator by spray coating.

A spray coating solution was prepared by placing 150.0 g of absolute ethyl alcohol in a container and adding 3.75 g of stearyl dimethyl ammonium chloride until solubilized. Thereafter 50.0 g of powdered gum guaiac was added with mixing for 15 minutes.

A fluidized bed apparatus (Aeromatic STREA-1) was charged with 441.25 g of crystalline sorbitol (USP tableting grade). About 250 ml of the spray coating solution was sprayed from the bottom of the apparatus at a flow rate of 3 ml/minute using a nozzle size of 1.10 mm and with atomizing air at 0.30 bar. for 1 hour and 45 minutes. The inlet temperature was 40° C. and the outlet temperature was 28° C. Thereafter, the coated product was dried for 20 minutes at 60° C. The yield was about 90%. The coated product was a free-flowing granular material.

A blender was charged with 490.0 g of the coated material and to this was added 10.0 g of submicron size talc. Thereafter the talc-containing coated granulation was dried 1 hour at 65° C. in a forced draft oven.

A peroxidase-like activity detection solution was prepared by dissolving 500 mg of the talc-containing coated granulation in 15 ml of reagent solution containing 5% w/v of a 30% hydrogen peroxide solution; 0.11% w/v citric acid (final solution pH 5.7–6.3); 0.25% w/v sodium citrate; 60% v/v of a methanol/ethanol solution (5 parts to 100 parts); 34.7% v/v water. Dissolution took place within thirty (30) seconds.

The effectiveness of this solution for detecting peroxidase-like activity was assessed by contacting previously prepared hemoglobin specimens with this solution. The hemoglobin specimens were prepared by taking diluted blood samples, drops of which were placed onto Whatman No. 1 filter paper. A drop of the invention's formulation was applied to the diluted blood sample and a distinct change of color from colorless to blue was observed.

EXAMPLE II–IV

These examples demonstrate the preparation of several free-flowing granular indicator materials and the use of such materials to determine peroxidase-like activity.

The procedure of Example I was followed except the relative amounts of sorbitol, gum guaiac, stearyl dimethyl benzyl ammonium chloride, talc and ethyl alcohol were varied in accordance with Table 1 below.

TABLE 1

| | Ex. II | Ex. III | Ex. IV |
|---|---|---|---|
| 1. Sorbitol | 441.25 g | 436.25 g | 445.00 g |
| 2. Gum guaiac | 50.00 g | 50.00 g | 50.00 g |
| 3. Stearyl dimethyl benzyl ammonium chloride (in solution) | 3.75 g | 3.75 g | 5.00 g |
| 4. Talc | 10.00 g | 15.00 g | 5.00 g |
| 5. Ethyl Alcohol (anhydrous) | 150.00 g | 150.00 g | 1045.00 g |

Each granular indicator formed in each case was readily soluble in the organic reagent and was subjected to the peroxidase-like activity test of Example I with similar results.

EXAMPLE V

In this Example, the procedure of Example I was repeated except that mannitol was substituted for the sorbitol of Example I. The amounts of ingredients are given in Table 2 below.

TABLE 2

| 1. Mannitol | 436.25 g |
|---|---|
| 2. Gum guaiac | 50.00 g |
| 3. Stearyl dimethyl benzyl ammonium chloride | 3.75 g |
| 4. Talc | 15.00 g |
| 5. Ethyl alcohol (anhydrous) | 150.00 g |

Solubility of the gum guaiac coated sorbitol in the organic reagent occurred within 30 seconds. Its effectiveness in determining peroxidase-like activity was similar to the indicator of Example 1.

The invention being thus described, it will be obvious that the same may be varied in many ways. Such variations are not to be regarded as a departure from the spirit and scope of the invention and all such modifications are intended to be included within the scope of the following claims.

We claim:

1. A free-flowing granular indicator material comprising a granular component selected from the group consisting of sorbitol, mannitol and mixtures thereof having gum guaiac coated thereupon, wherein said granular indicator material has increased solubility in an aqueous-organic indicator solution.

2. The free-flowing granular indicator of claim 1 wherein said gum guaiac is selected from the group consisting of resin guaiac, individual components of resin guaiac, guaiaretic acid, guaiacin and mixtures thereof.

3. The free-flowing granular material of claim 1 wherein said gum guaiac comprises from about 1.25% to 30% by weight of total granular material.

4. The free-flowing granular material of claim 1 which further comprises an antistatic agent.

5. The free-flowing granular material of claim 4 wherein said antistatic agent is a quaternary ammonium compound selected from the group consisting of stearyl dimethyl benzyl ammonium chloride, bis-(2-hydroxy-ethyl) octyl methyl ammonium para-toluene sulfonate, mink-amido-propyl dimethyl hydroxy-ethyl ammonium chloride, tetradecyl trimethyl ammonium bromide and a tallow polyamine quaternary ammonium compound.

6. The free-flowing granular material of claim 1 which further comprises a glidant.

7. The granular indicator material of claim 6 wherein said glidant is a submicron size material selected from the group consisting of talc, microcrystalline cellulose, powdered cellulose, calcium silicate, corn starch, sodium benzoate and calcium carbonate.

8. A test reagent system for detecting the presence of peroxidase-like activity which comprises:
(a) a free-flowing granular indicator material comprising a granular substrate selected from the group consisting of sorbitol, mannitol and mixtures thereof having gum guaiac coated thereon wherein the gum guaiac is present at a level of about 0.01% to about 3.0% based on the test reagent system; and
(b) an aqueous-organic reagent solution containing an organic solvent that is capable of solubilizing the indicator material and is present in an amount sufficient to keep the gum guaiac in solution, an oxidizing agent at a level of from about 0.15 to about 3.0% by weight of said solution and which is capable of oxidizing said indicator material in the presence of peroxidase-like activity, a buffer to maintain the pH of the solution within a range in which the indicator material changes color upon oxidation, and water in an amount sufficient to dissolve the oxidizing agent and buffer.

9. The test reagent system of claim 8 wherein said gum guaiac is selected from the group consisting of resin guaiac, individual components of resin guaiac, guaiaretic acid, guaiacin and mixtures thereof.

10. The test reagent of claim 8 wherein the oxidizing agent is an organic peroxide or an inorganic peroxide.

11. The test reagent of claim 8 wherein the organic solvent is selected from the group consisting of alcohols, ketones, and mixtures thereof.

12. The test reagent of claim 8 wherein the buffer is sufficient to maintain the pH of the solution in range of about 2.0 to about 8.0.

13. The test reagent of claim 8 wherein the indicator material further comprises an antistatic agent.

14. The test reagent of claim 13 wherein said antistatic agent is a quaternary ammonium compound selected from the group consisting of stearyl dimethylbenzylammoniumchloride, bis-(2-hydroxy-ethyl) octyl methyl ammonium para-toluene sulfonate, mink-amido-propyl dimethyl hydroxy-ethyl ammonium chloride, tetradecyl trimethyl ammonium bromide and a tallow polyamine quaternary ammonium compound.

15. The test reagent of claim 8 wherein the indicator material further comprises a glidant.

16. The test reagent of claim 15 wherein said glidant is a submicron size material selected from the group consisting of talc, microcrystalline cellulose, powdered cellulose, calcium silicate, corn starch, sodium benzoate and calcium carbonate.

* * * * *